United States Patent [19]
Combs

[11] Patent Number: 5,643,270
[45] Date of Patent: Jul. 1, 1997

[54] MULTI-PLANE CURVILINEAR SAW, GUIDE AND METHOD

[76] Inventor: C. Robert Combs, 708 Turf Ct., Lexington, Ky. 40502

[21] Appl. No.: 510,893

[22] Filed: Aug. 3, 1995

[51] Int. Cl.$^6$ .................................................. A61B 17/00
[52] U.S. Cl. .............................. 606/79; 606/86; 606/176; 606/179
[58] Field of Search .................... 606/79, 80, 81, 606/82, 84, 85, 86, 87, 88, 89, 96, 105.5, 176, 177, 178, 179; 128/898

[56] References Cited

U.S. PATENT DOCUMENTS

| | | | |
|---|---|---|---|
| 2,455,655 | 12/1948 | Carroll | 606/82 |
| 3,667,456 | 6/1972 | Charnley . | |
| 4,004,581 | 1/1977 | Heimke et al. . | |
| 4,069,824 | 1/1978 | Weinstock | 606/82 |
| 4,116,200 | 9/1978 | Braun et al. . | |
| 4,150,675 | 4/1979 | Comparetto | 606/85 |
| 4,273,117 | 6/1981 | Neuhauser . | |
| 4,284,080 | 8/1981 | Rehder . | |
| 4,718,413 | 1/1988 | Johnson . | |
| 5,049,149 | 9/1991 | Schmidt . | |
| 5,087,261 | 2/1992 | Ryd et al. | 606/82 |
| 5,100,267 | 3/1992 | Salyer . | |
| 5,176,685 | 1/1993 | Rayhack . | |
| 5,203,653 | 4/1993 | Kudla . | |
| 5,295,992 | 3/1994 | Cameron . | |
| 5,350,382 | 9/1994 | Armstrong . | |
| 5,496,325 | 3/1996 | McLees | 606/82 |

OTHER PUBLICATIONS

KaMing Li, MD et al., "Endoscopic Retrieval of Severed Flexor Tendons", Mar. 1995, *The Journal of Hand Surgery*, pp. 278–279.

*Primary Examiner*—Michael Buiz
*Assistant Examiner*—Mark S. Leonard
*Attorney, Agent, or Firm*—King And Schickli

[57] ABSTRACT

A multi-plane curvilinear saw, corresponding guide and related method are provided for shaping the end of a bone that forms one member of a joint, such as a bone in a digit. The finished end is hemispherical in shape so as to better engage the mating bone end. The saw includes a hollow, hemispherically shaped body with a row of arcuately disposed cutting teeth along an exposed edge of the front, and an open rear portion. A shank extends from the other side of the body for attachment to the chuck of a hand piece with a high-speed oscillating motion. The guide is formed from an elongated inverted channel with parallel curved slots in a terminal portion. The curvature of the slots corresponds to the curvature of the saw and the row of cutting teeth. The method includes the steps of securing the guide to the top of the digit above the joint and oscillating the saw, pitching forward and slightly tilting within the guide slots to shape and finish the bone end.

16 Claims, 2 Drawing Sheets

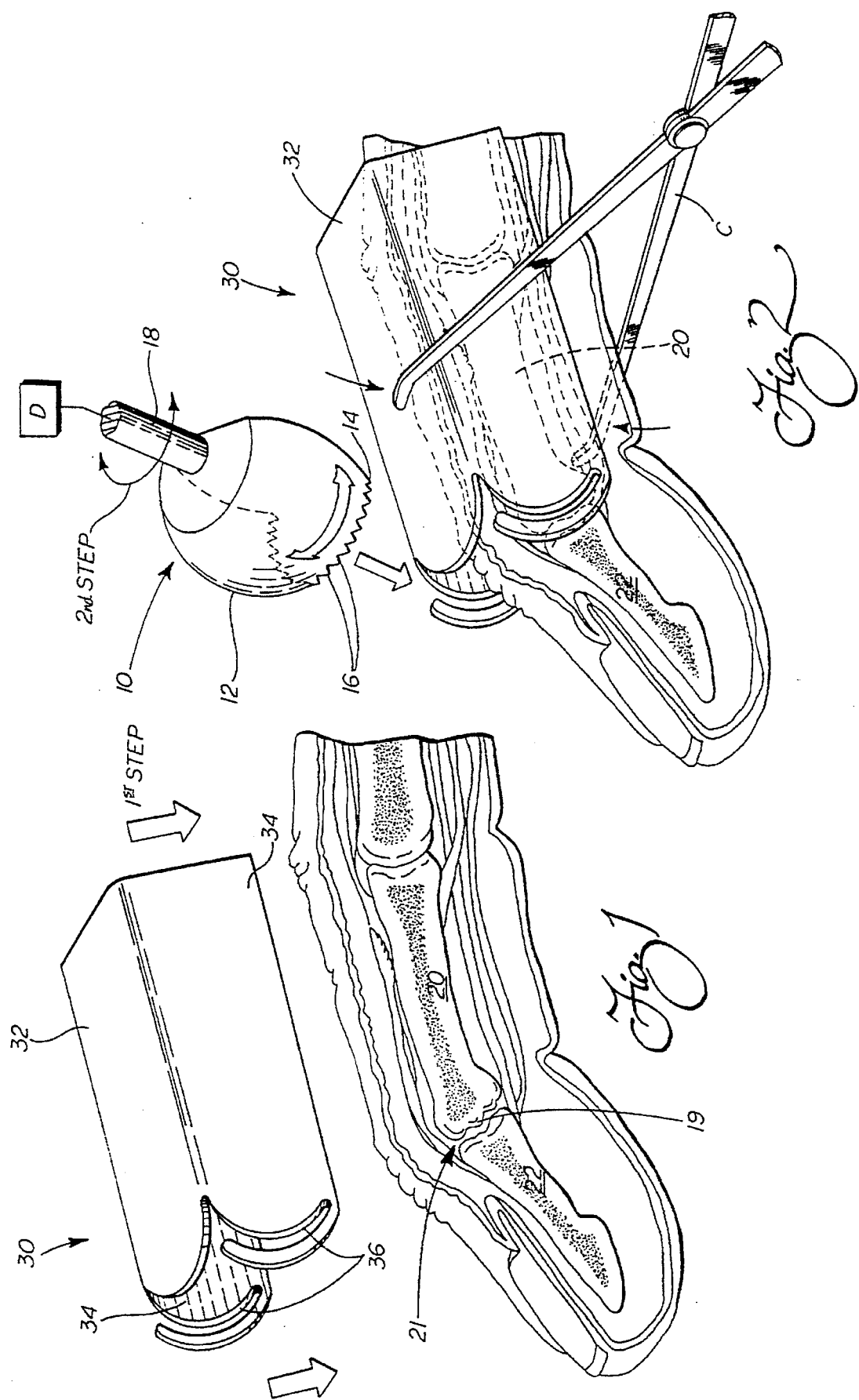

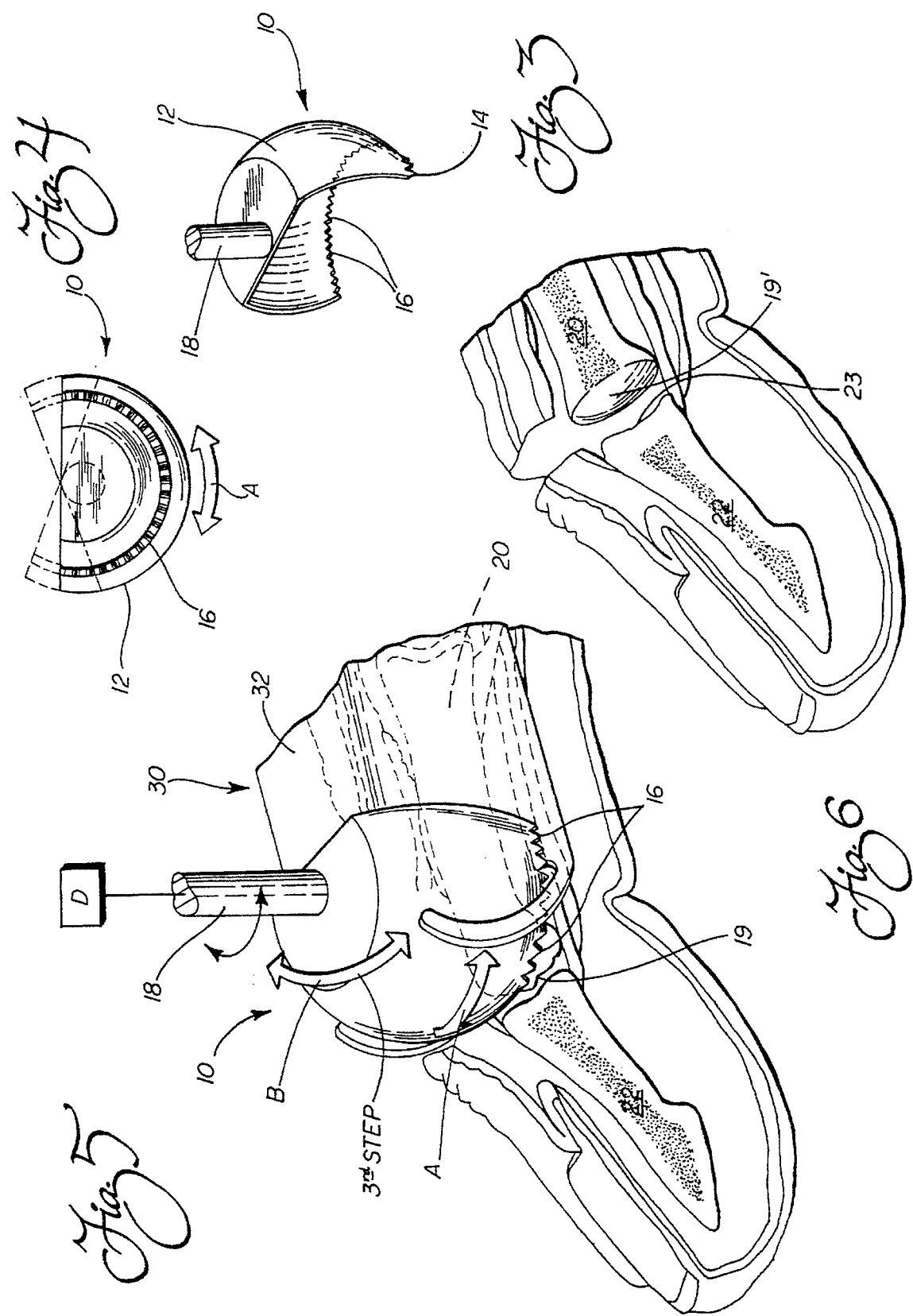

MULTI-PLANE CURVILINEAR SAW, GUIDE AND METHOD

TECHNICAL FIELD

The present invention relates generally to surgical instruments, and a corresponding method for preparing a joint for fusion; and more particularly, to a novel bone saw, corresponding guide and related method for rounding the end of a bone that forms one member of a joint in a digit.

BACKGROUND OF THE INVENTION

One of the first steps in a fusion procedure on a damaged bone joint is to prepare the surface of the bone ends for optimal engagement. Most commonly, the bone ends are sawed, and/or finished smooth, so as to be flat to create opposing planar surfaces that mate to form an angled miter-type joint. In cutting the bone ends to form this joint, the surgeon typically uses a flat reciprocating saw blade. A template or saw guide is also commonly used to align the blade to cut at the precise angle required.

Of particular interest with respect to creating such miter-type joints in a digit is illustrated as a part of the Joint Fixation System and Related Method, set forth in Applicant's co-pending U.S. Patent application, Combs, Ser. No. 08/510,721, filed Aug. 3, 1995, pending. In this prior application, I have illustrated and claimed a method and related surgical instruments/tools for preparing and stabilizing a joint in the finger or toe for fusion. More specifically, the instruments include a saw guide with linear guide slots for aligning a flat, reciprocating saw blade to make a planar cut on the end of the bone, such as the middle phalanx of the finger. This prior application thus addresses the need for a system and method of making flat cuts on the small bones of a digit.

Especially with a joint of a digit, such as the middle/distal phalanx joint in a finger, it is desirable in certain situations to form the end of one member of the joint into a rounded/spherical shape. This option is particularly favored to provide a better match between the two bones forming the joint. Also, providing a rounded end surface to at least one member, the opposing member may be positioned at the optimum angle for fusion. For example, when the first finger is being surgically repaired, the surgeon is able to select the best angle to provide maximum use with the thumb, such as to grasp and pick up items.

In the prior art, there are several surgical instruments, predominantly rotary milling tools/reamers that are specifically designed for cutting/smoothing the end of a large bone, such as the femur. These prior art tools are typically concave or cup-shaped with cutting protrusions on their outer edge and within their generally hemispherical interior to produce a full spherical or ball shape bone end.

One disadvantage with these tools is that their continuous hemispherical shape prevents them from accessing the bone end in its natural position. Instead, the bone must be severely dislocated to allow the end to be inserted into the cutting recess. This additional step of dislocating the bone increases both the complexity and the overall required time for the preparatory procedure for fusion. An example of a typical cup-shaped cutting tool is shown in U.S. Pat. No. 4,284,080 to Rehder, and a similar cutting tool is shown in U.S. Pat. No. 3,667,456 to Charnley.

Another disadvantage with the prior art surgical cutting instruments and tools for rounding a bone end is that none are designed to be used with a guide or template. As explained above, the saw guides of the prior art are designed solely for aligning flat, linearly reciprocating saw blades to make single plane cuts at a fixed angle. None of the prior art saw guides are designed for or capable of making multi-plane, rounded/spherical cuts. Examples of typical prior art saw guides are the U.S. patents to Johnson U.S. Pat. No. 4,718,413 and Rayhack U.S. Pat. No. 5,176,685.

Currently, the most common method for cutting the end of a small bone, such as the middle phalanx, into a mating shape is to use a reciprocating flat blade in a hand piece assembly. Generally, only substantially single plane, linear cuts can be reliably obtained to shape the bone end. This technique is very tedious and time-consuming, as the surgeon must slowly and carefully remove small shavings of the bone to insure that the proper angle and shape is obtained and that the bone is not unduly shortened. Without any external alignment or guidance, in real life it is inevitable that misshapen and unsymmetrical bone ends are often created. Furthermore, because the surgeon is manipulating the saw free-hand, slips of the blade and inadvertent cuts of delicate surrounding tissue are a constant possibility.

Thus, as demonstrated by the limitations of the prior art, there is a need identified for a multi-plane curvilinear saw, corresponding guide and related method that are specifically designed for cutting the ends of the small bones in the fingers or toes. This allows the surgeon to accurately, efficiently and safely perform the cutting procedure so as to provide a more efficient match of the bone ends.

SUMMARY OF THE INVENTION

Accordingly, it is a primary object of the present invention to provide a novel and improved multi-plane curvilinear saw, guide and related method that are particularly adapted for cutting the bones in a digit, the concepts and features being designed to overcome the limitations of the prior art.

Another object of the present invention is to provide a multi-plane curvilinear saw that is specifically adapted for shaping the end of a bone in a digit into a rounded/spherical surface without requiring the bone to be dislocated.

It is another object of the present invention to provide a multi-plane curvilinear saw that is used with a corresponding guide to efficiently and accurately make the desired cut and thereby eliminate the need for free hand manipulation of the saw.

It is yet another object of the present invention to provide a saw guide that includes curved slots for directing a multi-plane curvilinear saw to make a multiple plane, rounded cut on the end of a bone in a digit, and also for protecting the surrounding tissue from the cutting teeth of the saw.

It is still another object of the present invention to provide an improved bone cutting method for creating a rounded bone end, wherein consistent precision and accuracy are achieved.

It is yet another object of the present invention to provide an improved bone cutting method for creating a rounded bone end, the method having steps designed to minimize the required time for the cutting procedure and substantially eliminating the risk of inadvertent cuts of surrounding tissue.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, a novel and improved multi-plane curvilinear bone saw, corresponding guide and related method are provided. The saw is particularly designed for cutting the end of a bone to create a substantially rounded shape, and is specifically adapted for cutting the end of one member of the joint of a digit, such as between the middle and distal phalanx in a finger.

The multi-plane curvilinear saw includes a hemispherically-shaped body that has an arcuate exposed edge on one side. Cutting means are provided along this edge, with the preferred embodiment utilizing a plurality of cutting teeth aligned in a single, arcuate row and projecting downwardly from the edge. On the side of the body opposite from the cutting teeth is a connection means for connecting the body to a power hand piece. Preferably, the connection means comprises a shank extending from the body, and the power hand piece operates in a high-speed oscillating fashion; a chuck on the hand piece being adapted to accept and secure the shank. The hand piece should be small enough to be easily handled with one hand to allow the surgeon to comfortably and accurately manipulate the attached saw.

In an important aspect of the present invention, the body of the saw is substantially hollow with an open rear portion to provide open space adjacent to and away from the cutting teeth along the arcuate exposed edge. Advantageously, this unique construction allows the curved row of cutting teeth to trace a multi-plane curvilinear path as the saw body is translated across the bone end. This allows the bone end to be cut into a substantially rounded shape with an ease and efficiency heretofore unattainable.

In a further important aspect of the present invention, the saw performs the above-described cutting operation without requiring the bone to be dislocated or repositioned over a substantial distance. Advantageously and unexpectedly, the unique construction of the multi-plane curvilinear saw of the present invention enables it to access the end of the middle phalanx while the bone remains substantially in its natural position. This greatly simplifies the cutting procedure and correspondingly reduces the required time for the procedure.

To align the multi-plane curvilinear saw to cut the bone end, a novel and improved saw guide is also provided. The saw guide comprises an elongated inverted channel with the sides of the channel formed by parallel plates depending downwardly from the top surface. A curved slot is formed in a terminal portion of each of the plates. The slots are open at the top to allow insertion of the cutting teeth and body of the saw. The equidistant spaced edges of the slots guide the cutting teeth along a multi-plane curvilinear path across or laterally, as well as up and down, on the bone end.

Advantageously, by using the saw guide in combination with this multi-plane curvilinear saw of the present invention, the surgeon is assured of making consistently precise and accurate cuts on the bone end. The surgeon can select the perfect angled position of the joint to be fused, both laterally (side to side) and up and down. Additionally, using the saw guide to automatically position the cutting teeth allows the cutting procedure to be performed quickly and efficiently. The saw guide faithfully restricts the movement of the cutting teeth to the path defined by the curved slots. In this manner, the saw guide makes a smooth, consistent cut every time, and substantially eliminates the possibility of inadvertent slips and damaging cuts to the delicate tissue surrounding the bone end.

In accordance with the related method of cutting the end of a bone into a rounded surface, the first step involves positioning the saw guide on the digit and aligning the curved slots with the bone end to be cut. The saw guide is affixed to the digit by any suitable means, such as a standard surgical clamp. The multi-plane curvilinear saw is secured in the chuck of the high-speed oscillating hand piece. In the second step of the method, the hand piece is activated to provide the desired oscillatory motion to the cutting teeth of the saw.

In the third step of the method, the saw is bodily pitched forwardly and moved downwardly between the spaced edges of the slots in the saw guide, with the slots leading the cutting teeth along a multi-curvilinear path across the bone end. The saw can also be delicately translated, tilted and/or rotated to a limited degree about the end of the bone by the surgeon to make the exact and precise hemispherical shaped cut desired. This oscillatory, as well as bodily movement of the multi-plane curvilinear saw within the slots is maintained until the desired rounded shape of the bone end is obtained.

As described above, the improved bone cutting method of the present invention allows a surgeon to consistently create a uniformly rounded surface on a bone end. The present method also significantly reduces the time required for the finished procedure as compared to the methods of the prior art; and in particular, the present method is much more exact and less time consuming than trying to use the free hand method of rounding the bone end by using a flat-blade reciprocating saw without a guide or template. Further, as described above, the use of a saw guide in the present method protects the surrounding tissue from inadvertent cuts by the cutting teeth.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modifications in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification, illustrate several aspects of the present invention, and together with the description serve to explain the principles of the invention. In the drawings:

FIG. 1 is a perspective view of the saw guide of the present invention and the first step of the related method showing the guide being installed over a damaged joint of a digit, and in particular between a middle and distal phalanx bone in a finger;

FIG. 2 is a perspective view of the multi-plane curvilinear saw of the present invention and the second step of the related method showing the saw being oscillated by a powered hand piece and being aligned over and lowered toward the slots in the saw guide;

FIG. 3 is an overall perspective view of the multi-plane curvilinear saw showing the rear cutout portion;

FIG. 4 is a bottom view of the multi-plane curvilinear saw depicting by dash/dot line and action arrow the oscillatory motion of the saw;

FIG. 5 a perspective view of the third step of the present invention showing by action arrow the multi-plane curvilinear saw being pitched forwardly, moved downwardly and oscillated within the slots of the saw guide so that the cutting teeth trace the multi-plane curvilinear path across the end of the middle phalanx; and FIG. 6 is a cut-away partial view showing the finished end of the middle phalanx having the desired rounded shape for mating with the distal phalanx.

Reference will now be made in detail to the present preferred embodiment of the invention, an example of which is illustrated in the accompanying drawings.

DETAILED DESCRIPTION OF THE PREFERRED EMBODIMENT

Reference is now made generally to FIGS. 1–6 which illustrate a novel and improved multi-plane curvilinear bone saw, guide and related method for cutting the end of a bone into a rounded shape. The instruments and method are particularly adapted for preparing joints in a digit for fusion, and more specifically for rounding the end of the middle phalanx in a finger to create an ideal mating surface for the opposing end of the distal phalanx.

With reference now to FIGS. 2 and 3, the multi-plane curvilinear saw of the present invention, generally designated by the reference numeral 10, comprises a hemispherically-shaped body 12 with an arcuate exposed edge 14 on one side in the front and a cutout portion around the rear. Disposed along the arcuate exposed edge 14 are cutting means that contact and cut the bone end. In the preferred embodiment, the cutting means comprise a plurality of cutting teeth 16 arranged in a single row and extending downwardly from the edge 14.

On the side of the body 12 opposite from the arcuate exposed edge 14, the saw 10 includes a connection means for securing the body 12 to a power means. In the preferred embodiment, the connection means comprises an elongated shank 18 that extends from the body 12. The power means preferably comprises a hand piece or drill D that includes a chuck (not shown) that accepts and secures the shank 18. The hand piece D provides a high speed oscillating motion to the saw 10, as illustrated by action arrow A in FIGS. 4 and 5.

In accordance with an important aspect of the present invention, the body 12 of the saw 10 is substantially hollow along with having an open rear portion to provide the hemispherical shape, so as to provide open space adjacent to and behind the cutting teeth 16. As best illustrated in FIG. 5, the hollow construction of the body 12 allows the saw 10 to be oscillated, as well as freely translated and bodily rotated about the end 19 of the middle phalanx 20. Consequently, the cutting teeth 16 are able to follow an arcuate/spherical path around the bone end 19 without the supporting structure of the body 12 interfering with the travel of the teeth 16. Advantageously, this unique construction allows a rounded cut to be made with much greater ease, precision and speed than with the flat reciprocating saws of the prior art. Furthermore, the arcuate cutting surface defined by the curved cutting teeth 16 consistently yields an evenly curved surface on the bone end; a result that is exceedingly difficult to obtain with a flat saw.

In another important aspect of the present invention, the unique hollow construction of the hemispherically-shaped body 12 allows the cutting teeth 16 to access the end 19 of the middle phalanx 20 without requiring the end 19 to be dislocated or repositioned. As shown in FIG. 5, the saw 10 performs the above-described cutting operation while the middle phalanx 20 remains in its natural position opposite the distal phalanx 22. Advantageously, by eliminating the necessity of dislocating the middle phalanx 20, the multicurvilinear saw 10 of the present invention simplifies the overall cutting procedure and significantly reduces the time required for the procedure.

As illustrated in FIGS. 1, 2 and 5, a saw guide, generally represented by the reference numeral 30, is also provided to define an arcuate path for the cutting teeth 16 of the multi-plane curvilinear saw 10 to follow. The guide 30 is in the form of an elongated inverted channel comprising a horizontal upper surface 32 and parallel plates 34 depending downwardly at right angles. Dual curved slots 36 are formed in a terminal portion of the plates 34. The slots 36 are open at their top to receive the cutting teeth 16 and the front of the body 12 of the saw 10.

As shown in FIG. 2, the saw guide 30 is positioned over the middle phalanx 20 such that the curved slots 36 define an arcuate path across the end 19 of the middle phalanx 20. The guide 30 is secured to the finger by any suitable means, such as a surgical clamp C (see dashed line outline). Once properly positioned and secured, the spaced edges of the slots 36 preferably allow free oscillatory and rotational movement of the teeth 16 while simultaneously restricting translational movement, thereby insuring that a uniformly curved cut is achieved.

Advantageously, the saw guide 30 allows a surgeon to make a consistently precise multiple plane cut on the end 19 of the middle phalanx 20 that defines a plurality of curvilinear paths or lines across it. Using the saw guide 30 to automatically position the saw 10 also further reduces the required time for the cutting procedure, as no separate or additional alignment of the saw 10 is required. As the hand piece pitches forward for cutting, the surgeon can also bodily move or tilt the hand piece D a slight distance across the top of the finger within the confining limits of the slots 36 for precise adjustment of the cut, as desired. However, in an important aspect of the present invention, the saw guide 30 does protect the delicate tendons and other tissue adjacent to the bone end 19 by restricting the travel of the cutting teeth 16 to the path generally defined by the curved slots 36. In this manner, the saw guide 30 provides maximum protection from inadvertent and damaging cuts of the surrounding tissue.

The present invention also includes a novel and improved method for cutting the end of a bone into a substantially rounded shape. As shown in FIGS. 1, 2 and 5, the method of the present invention is particularly adapted for cutting the end 19 of the middle phalanx 20 that forms one member of the middle/distal phalanx joint, generally represented by the reference numeral 21. As these figures make apparent, the preferred embodiment of the present method contemplates the use of the novel saw guide 30 and multi-plane curvilinear saw 10 of the present invention. However, it should be understood that the broader concepts of the present invention include the use of method relative to other digits, such as toes, as well as use with other and different instruments in practicing the present method.

With reference now to FIGS. 1 and 2, the improved cutting method begins with a first step of positioning and lowering the saw guide 30 over the middle phalanx 20 such that the curved slots 36 define an arcuate path across the bone end 19. The guide 30 is secured to the finger by any suitable means, such as a standard surgical clamp C (shown in dashed line outline in FIG. 2).

The second step of the method involves activating the high-speed oscillating hand piece D to provide motion to the cutting teeth 16 of the saw 10. As described above and illustrated by the action arrows in FIGS. 2 and 4, the drill provides oscillatory movement to the cutting teeth 16 on the front of the body 12, such that the teeth oscillate about an axis of rotation defined by the shank 18.

With reference now to FIGS. 4 and 5, in the third step of the method the multi-plane curvilinear saw 10 is bodily moved downwardly within the curved slots 36 of the saw guide 30. The curvature of the slots 36 guides the saw 10 to pitch forward in the direction of action arrow B as the saw 10 is moved downwardly. At the same time, the oscillatory motion of the saw 10, designated by the action arrow A, traces an arcuate cutting path in dual planes across (see arrow A), as well as up and down (see arrow B). Advantageously, the unique combination of the oscillatory motion of the teeth 16, and the forward pitching and minor lateral tilting motions of the hand piece D, results in accurately tracing the multi-plane curvilinear/hemispherical cutting path across the end 19 of the middle phalanx 20. To complete the cutting procedure, the movement of the saw 10 along this cutting path is maintained until the entire cross section of the bone is cut.

As described above, the improved method of the present invention allows a surgeon to consistently and safely cut the end of a bone into a smooth and uniformly rounded surface. The three simple steps, including especially the use of the saw guide 30 to guide the cutting step, comprise a quick and efficient cutting method that significantly reduces the overall required time for the procedure as compared to the known methods of the prior art. Furthermore, the method of the present invention provides maximum protection from inadvertent cuts by utilizing the saw guide 30 to generally restrain the movement of the cutting teeth 16 to the desired cutting path. This virtually eliminates the possibility of damaging any delicate surrounding tissue.

As illustrated in FIG. 6, the method of the present invention yields a uniformly rounded end 19' with a hemispherical profile that ideally mates with the opposing surface 23 of the distal phalanx 22. Preferably, the opposing surface 23 has a concave profile that may be formed, for example, by using a smoothing disc similar to the one disclosed in Applicant's co-pending application, Combs, Ser. No. 08/510,721, pending; the smoothing disc being modified to have a convex cutting surface to produce the desired concave shape. It should be appreciated, however, that the opposing surface 23 may be more or less finished in any other suitable profile, in order to provide the improved fusion of the bone ends.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

I claim:

1. A multi-plane curvilinear saw for cutting an end of a bone in response to activation by power means, and particularly adapted for providing a substantially rounded shape on the end of a bone that forms one member of a joint in a digit, comprising:

a substantially hollow, hemispherically shaped body having an arcuate exposed edge on one side;

connection means on a side opposite from said one side for connecting said body to said power means to provide activation of said arcuate exposed edge; and cutting means disposed along said arcuate exposed edge;

whereby said cutting means upon being activated in response to said power means and positioned to engage said bone end is operative to create said rounded shape.

2. The multi-plane curvilinear saw of claim 1, wherein said hemispherically shaped body includes a front on which the cutting means is provided and a substantially open rear portion away from said arcuate exposed edge to provide clearance so that said cutting means may be freely moved to cut said rounded shape.

3. The multi-plane curvilinear saw of claim 1, wherein said connection means includes a shank extending from said opposite side.

4. The multi-plane curvilinear saw of claim 1, wherein said cutting means includes a plurality of cutting teeth.

5. The multi-plane curvilinear saw of claim 4, wherein said cutting teeth are arranged in a single, curved row.

6. The multi-plane curvilinear saw of claim 1, wherein said power means is a hand piece providing oscillatory motion.

7. A saw guide for aligning a multi-plane curvilinear saw to cut the end of a bone, and particularly adapted for aligning a multi-plane curvilinear saw to provide a substantially rounded shape on the end of a bone that forms one member of a joint in a digit, comprising:

an elongated inverted channel having an upper surface and parallel plates depending downwardly from said surface; and a curved slot in a terminal portion of each of said parallel plates, said slot having spaced edges and being open at its top;

whereby said spaced edges guide said multi-plane curvilinear saw to engage said bone end and create said rounded shape.

8. The saw guide of claim 7, wherein said multi-plane curvilinear saw includes a front on which the cutting means is provided and a substantially open rear portion away from an arcuate exposed edge to provide clearance so that said cutting means may be freely moved to cut said rounded shape.

9. A method for cutting the end of a bone, particularly adapted for providing a substantially rounded shape on the end of a bone that forms one member of a joint in a digit, the method comprising the steps of:

providing a multi-plane curvilinear saw having a cutting means;

providing a power means for activating said cutting means;

providing a saw guide having curved slots;

positioning said saw guide over said bone end;

activating said power means to provide cutting motion to said cutting means; and bodily moving said multi-plane curvilinear saw downwardly within said slots around the bone end to engage said cutting means against said bone end;

whereby said bone end is cut to form said rounded shape.

10. The method for cutting the end of a bone of claim 9, further comprising the step of securing said saw guide to the top of said digit.

11. The method for cutting the end of a bone of claim 9, wherein the step of providing a multi-plane curvilinear saw having a cutting means includes providing a substantially hollow, hemispherically shaped body having an arcuate exposed edge on one side, said edge including said cutting means; and connection means on a side opposite from said one side for connecting said body to said power means.

12. The method for cutting the end of a bone of claim 9, wherein the step of providing a saw guide having curved slots includes providing an elongated inverted channel having:

an upper surface;

parallel plates depending downwardly from said surface; and a curved slot in a terminal portion of each of said parallel plates, said slot having spaced edges and being open at its top, said slot having a curvature that corresponds to the curvature of said multi-plane curvilinear saw and said cutting means.

13. The method for cutting the end of a bone of claim 9, wherein the step of providing a power means for activating said cutting means includes moving said saw with oscillatory motion.

14. The method for cutting the end of a bone of claim 9, wherein the step of bodily moving said multi-curvilinear saw is maintained until said bone end is cut to form said rounded shape.

15. The method for cutting the end of a bone of claim 14, wherein the bodily moving step includes pitching the power means forward for cutting by said saw.

16. The method for cutting the end of a bone of claim 14, wherein the bodily moving step includes slightly tilting the power means to one side for more precise control when needed.

* * * * *